United States Patent
Kang et al.

(10) Patent No.: US 10,861,153 B2
(45) Date of Patent: Dec. 8, 2020

(54) USER TERMINAL APPARATUS AND CONTROL METHOD THEREOF

(71) Applicant: SAMSUNG ELECTRONICS CO., LTD., Suwon-si (KR)

(72) Inventors: Seong-min Kang, Seoul (KR); Heung-woo Han, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/517,267

(22) Filed: Jul. 19, 2019

(65) Prior Publication Data

US 2019/0340759 A1   Nov. 7, 2019

Related U.S. Application Data

(63) Continuation of application No. 15/361,119, filed on Nov. 25, 2016, now Pat. No. 10,521,903.

(30) Foreign Application Priority Data

Nov. 25, 2015   (KR) .................. 10-2015-0165794

(51) Int. Cl.
*G06K 9/00* (2006.01)
*G06T 7/00* (2017.01)
(Continued)

(52) U.S. Cl.
CPC .......... *G06T 7/0012* (2013.01); *G06F 19/321* (2013.01); *G06F 19/3475* (2013.01);
(Continued)

(58) Field of Classification Search
CPC .............. G06F 19/321; G06F 19/3475; G06K 2209/17; G06K 9/00671; G06K 9/6267; G09B 19/0092
See application file for complete search history.

(56) References Cited

U.S. PATENT DOCUMENTS 8,345,930 B2   1/2013   Tamrakar et al.
8,605,952 B2   12/2013   Boushey
(Continued)

FOREIGN PATENT DOCUMENTS

EP   2741292 A1   6/2014
JP   2014-203387 A   10/2014
(Continued)

OTHER PUBLICATIONS

Communication dated Dec. 17, 2018, issued by the European Patent Office in counterpart European Patent Application No. 16868920.6.
(Continued)

*Primary Examiner* — Ian L Lemieux
(74) *Attorney, Agent, or Firm* — Sughrue Mion, PLLC

(57) ABSTRACT

A user terminal apparatus is provided. The user terminal apparatus includes a camera configured to obtain a captured image; a storage configured to store a food intake history; a processor configured to extract a food image from the captured image and determine a food type of a food item included in the captured image based on feature information of the extracted food image and the previously stored food intake history; and a display configured to display relevant information about the determined food type.

3 Claims, 19 Drawing Sheets

(51) Int. Cl.
  *G16H 20/60* (2018.01)
  *G16H 30/20* (2018.01)
  *G06F 19/00* (2018.01)
  *G06K 9/62* (2006.01)
  *G09B 19/00* (2006.01)

(52) U.S. Cl.
  CPC ....... *G06K 9/00671* (2013.01); *G06K 9/6267* (2013.01); *G09B 19/0092* (2013.01); *G16H 20/60* (2018.01); *G16H 30/20* (2018.01); *G06K 2209/17* (2013.01); *G06T 2200/24* (2013.01)

(56) References Cited

U.S. PATENT DOCUMENTS

| | | | |
|---|---|---|---|
| 8,625,889 B2 | 1/2014 | De Oliveira et al. | |
| 9,703,928 B2 | 7/2017 | Mochizuki | |
| 9,977,980 B2* | 5/2018 | Joshi | G06F 16/583 |
| 10,102,342 B1* | 10/2018 | Vleugels | G16H 20/60 |
| 2003/0076983 A1 | 4/2003 | Cox | |
| 2006/0195858 A1 | 8/2006 | Takahashi et al. | |
| 2008/0159622 A1 | 7/2008 | Agnihotri et al. | |
| 2008/0247612 A1 | 10/2008 | Reber | |
| 2010/0111383 A1 | 5/2010 | Boushey et al. | |
| 2010/0332571 A1 | 12/2010 | Healey | |
| 2011/0318717 A1 | 12/2011 | Adamowicz | |
| 2012/0170801 A1* | 7/2012 | De Oliveira et al. | G06T 7/90 382/103 |
| 2013/0027424 A1 | 1/2013 | Mochizuki | |
| 2013/0260345 A1 | 10/2013 | Puri et al. | |
| 2014/0063180 A1 | 3/2014 | Sharma | |
| 2014/0147829 A1 | 5/2014 | Jerauld | |
| 2014/0170608 A1 | 6/2014 | Ting | |
| 2014/0214446 A1 | 7/2014 | Nusbaum et al. | |
| 2014/0349256 A1 | 11/2014 | Connor | |
| 2014/0350353 A1* | 11/2014 | Connor | G06K 9/00355 600/301 |
| 2015/0168365 A1* | 6/2015 | Connor | G06F 19/3475 356/51 |
| 2015/0170002 A1 | 6/2015 | Szegedy et al. | |
| 2015/0228062 A1 | 8/2015 | Joshi | |
| 2015/0235562 A1 | 8/2015 | Klein | |
| 2016/0063734 A1* | 3/2016 | Divakaran | G06K 9/4642 382/110 |
| 2016/0070960 A1 | 3/2016 | Aizawa et al. | |
| 2016/0112684 A1* | 4/2016 | Connor | G06T 7/0004 348/158 |
| 2017/0061821 A1 | 3/2017 | Choi | |
| 2017/0220772 A1* | 8/2017 | Vleugels | A61B 5/4866 |
| 2017/0277863 A1* | 9/2017 | Subra | G06T 11/001 |
| 2017/0323481 A1* | 11/2017 | Tran | G06K 9/00771 |
| 2019/0192073 A1* | 6/2019 | Shi | G06F 3/015 |
| 2019/0295440 A1* | 9/2019 | Hadad | G06F 40/216 |
| 2020/0117954 A1* | 4/2020 | Jiang | G06N 3/0454 |
| 2020/0152312 A1* | 5/2020 | Connor | A61B 5/0077 |

FOREIGN PATENT DOCUMENTS

| | | |
|---|---|---|
| KR | 10-2005-0003610 A | 1/2005 |
| KR | 10-1375018 B1 | 3/2014 |
| KR | 10-2015-0018759 A | 2/2015 |
| KR | 10-2015-0029257 A | 3/2015 |
| WO | 2007/069118 A2 | 6/2007 |
| WO | 2014/160298 A1 | 10/2014 |

OTHER PUBLICATIONS

Communication dated Jun. 27, 2018, issued by the European Patent Office in counterpart European Application No. 16868920.6.
International Search Report dated Jan. 31, 2017, issued by the International Searching Authority in counterpart International Patent Application No. PCT/KR2016/013673 (PCT/ISA/210).
Written Opinion dated Jan. 31, 2017, issued by the International Searching Authority in counterpart International Patent Application No. PCT/KR2016/013673 (PCT/ISA/237).
Summons to Oral Proceedings dated May 28, 2019 issued by the European Patent Office in European Patent Application No. 16868920.6.
Office Action dated Jan. 31, 2018 issued by the USPTO in parent U.S. Appl. No. 15/361,119.
Office Action dated Jul. 13, 2018 issued by the USPTO in parent U.S. Appl. No. 15/361,119.
Office Action dated Dec. 11, 2018 issued by the USPTO in parent U.S. Appl. No. 15/361,119.
Office Action dated Feb. 26, 2019 issued by the USPTO in parent U.S. Appl. No. 15/361,119.
Communication dated Oct. 14, 2019, issued by the European Patent Office in counterpart European Application No. 16 868 920.6.
Communication dated Jan. 9, 2020, issued by the European Patent Office in counterpart European Application No. 16 868 920.6.

* cited by examiner

FIG. 3

<milk>

| FOOD TYPE | WEIGHT |
|---|---|
| Soy milk | 10 |
| Whole milk | 7 |
| Low-fat milk | 4 |
| Banana milk | 1 |
| Strawberry milk | 0 |

USER TERMINAL APPARATUS AND CONTROL METHOD THEREOF

CROSS-REFERENCE TO RELATED APPLICATIONS

This application is a continuation of U.S. patent application Ser. No. 15/361,119 filed on Nov. 25, 2016, which claims priority from Korean Patent Application No. 10-2015-0165794, filed on Nov. 25, 2015 in the Korean Intellectual Property Office, the disclosure of which is incorporated herein by reference in its entirety.

BACKGROUND

1. Field

Apparatuses and methods consistent with exemplary embodiments relate to a user terminal apparatus and a control method thereof, and more particularly, to a user terminal apparatus capable of managing eating habits and health of a user, and a control method thereof.

2. Description of the Related Art

Obesity rates are on the rise and a need for management of eating habits is also increasing. Helping people maintain their health and fitness is one of the central goals of the healthcare industry, and various programs for improving diet and lifestyle have been developed to help people achieve these goals.

In order to improve eating habits, it is necessary to accurately monitor one's dietary intakes. For example, if types of food, amounts, calories, an intake time, etc. of ever meal a person eats during a day or a period are known, it is possible to accurately estimate how much food has been eaten, how much exercise is required to burn the calorie intake, etc.

As mobile devices such as smart phones become more prevalent, various application services have been introduced to help managing the diet. Examples of these applications include "S-Health," "Noom diet," etc.

However, because users have to manually select or input information related to type, amount, intake time, etc. of food that the users eat by entering text in such conventional applications, it is often cumbersome and inconvenient for the user to execute applications and input the above-described information after every meal.

Accordingly, a method for users to more easily manage food that users eat is needed.

SUMMARY

Exemplary embodiments overcome the above disadvantages and other disadvantages not described above. Also, an exemplary embodiment is not required to overcome the disadvantages described above, and an exemplary embodiment may not overcome any of the problems described above.

Exemplary embodiments provide a user terminal apparatus that allows a user to conveniently input food that the user eats through recognition of an image and a control method thereof.

According to an aspect of an exemplary embodiment, there is provided a user terminal apparatus including: a camera configured to obtain a captured image; a storage configured to store a food intake history; a processor configured to extract a food image from the captured image and determine a food type of a food item included in the captured image based on feature information of the extracted food image and the previously stored food intake history; and a display configured to display relevant information about the determined food type.

The processor may apply a weight to each food type based on the food intake history, and, if the food item is determined to be one of a plurality of different food types, determine the food item included in the captured image to be of a food type having a highest weight among the plurality of different food types.

The food intake history may include kinds food types that have been eaten by a user and respective intake frequencies associated with the food types, and the processor may apply the weight to each food type in accordance with an order of intake frequency and store the food intake history in the storage.

The processor may control the display to display a list of food types determined based on the feature information of the extracted food. The list may be sorted in order of weight. The processor may determine the extracted food image to be of a food type selected from the list according to a user input.

The processor may store the captured image in the storage, and, if a preset event occurs, select captured images that include the food image from captured images stored in the storage. The processor may display, on the display, a user interface (UI) in a timeline in which the selected captured images are aligned and displayed in order of a capturing time.

The relevant information may include at least one of the determined food type and calorie information.

The processor may update the food intake history according to at least one of a user input and a result of the determination.

If a plurality of food images are extracted from the captured image, the processor may provide a UI for selecting at least one of the extracted plurality of food images and determine the food type of the selected food image through the UI.

The processor may calculate and display a calorie amount that a user has eaten from an amount of food included in the captured image, the amount of food being input by the user, and store the input amount of food as information for determining an amount of food of a same food type as the determined food type.

According to an aspect of another exemplary embodiment, there is provide a user terminal apparatus including: a camera configured to obtain a captured image; a communication interface configured to communicate with an external server storing a food intake history; a processor configured to extract a food image from the captured image, transmit feature information of the extracted food image to the external server, and receive, from the external server, relevant information about a food type determined by the external server based on the feature information of the extracted food image and the food intake history; and a display configured to display the received relevant information.

According to an aspect of another exemplary embodiment, there is provided a control method of a user terminal apparatus including: obtaining a captured image; extracting a food image from the captured image; determining a food type of a food item included in the captured image based on feature information of the extracted food image and a previously stored food intake history; and displaying relevant information about the determined food type.

The method may further include applying a weight to each food type based on the previously stored food intake history. The estimating may include: if the food item is determined to be one of a plurality of different food types, determining the food item included in the captured image to be of a food type having a highest weight among the plurality of different food types.

The food intake history may include food types that have been eaten by a user and respective intake frequencies associated with the food types. The applying of the weight may include: applying the weight to each food type in accordance with an order of intake frequency, and storing the food intake history.

The determining may include: displaying a list of food types determined based on the feature information of the extracted food. The list may be sorted in order of weight. The extracted food image may be determined to be of a food type selected from the list according to a user input.

The method may further include: storing the captured image. The displaying may include: if a preset event occurs, selecting captured images that include the food image from the stored captured images; and displaying a user interface (UI) in a time line in which the selected captured images are aligned and displayed in order of a capturing time.

The relevant information may include at least one of the determined food type and calorie information.

The method may further include: updating the food intake history according to at least one of a user input and a result of the determination.

The determining may include: if a plurality of food images are extracted from the captured image, providing a UI for selecting at least one of the extracted plurality of food images, and determining the food type of the selected food image through the UI.

The displaying may further include: calculating and displaying a calorie amount that a user has eaten from an amount of food included in the captured image, the amount of food being input by the user; and storing the input amount of food as information for determining an amount of food of a same food type as the determined food type.

According to an aspect of another exemplary embodiment, there is provided a control method of a user terminal apparatus including: obtaining a captured image; extracting a food image from the captured image; transmitting feature information of the extracted food image to an external server storing a food intake history; receiving, from the external server, relevant information about a food type determined by the external server based on the feature information of the extracted food image and the food intake history; and displaying the received relevant information.

As described above, according to various exemplary embodiments of the present disclosure, a user may more conveniently input information about food that the user eats to an application executed in a user terminal apparatus, and user customized information for each user may be provided.

BRIEF DESCRIPTION OF THE DRAWINGS

The above and/or other aspects will be more apparent by describing certain exemplary embodiments with reference to the accompanying drawings, in which:

FIG. 3 is a diagram illustrating a method for applying weights to food types according to an exemplary embodiment;

DETAILED DESCRIPTION OF THE EXEMPLARY EMBODIMENTS

Exemplary embodiments will be described below in more detail with reference to the accompanying drawings.

Figure 1:
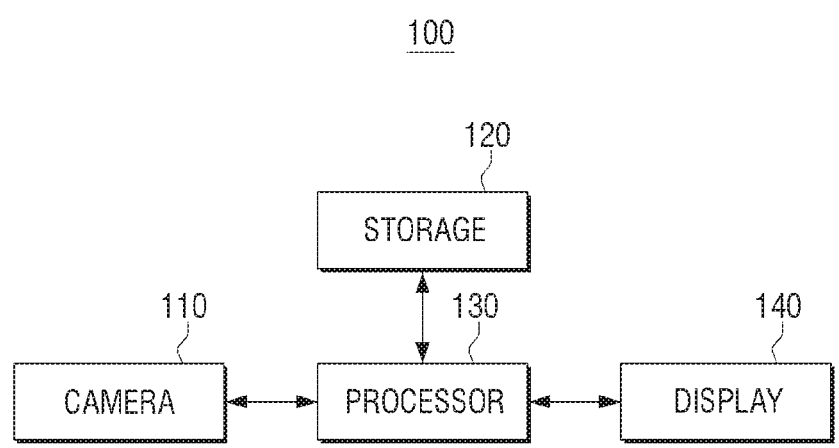
FIG. 1 is a schematic block diagram illustrating a configuration of a user terminal apparatus according to an exemplary embodiment.

FIG. 1 is a schematic block diagram illustrating a configuration of a user terminal apparatus 100 according to an exemplary embodiment.

The user terminal apparatus 100 according to an aspect of an exemplary embodiment may be a mobile electronic apparatus that includes a camera module. For example, the user terminal apparatus 100 may be a smart phone, a tablet personal computer (PC), a mobile phone, a conference phone, an e-book reader, a laptop PC, a netbook computer, a personal digital assistant (PDA), a portable multimedia player (PMP), an MP3 player, a global positioning system (GPS) navigation device, a camera, or a wearable device. The wearable device may be a head mounted device (HMD) such as electronic glasses, an appcessory, a smart watch, etc. However, it will be obvious to one of ordinary skill in the art that the user terminal apparatus 100 is not limited to the above-described apparatuses.

As shown in FIG. 1, the user terminal apparatus 100 according to an exemplary embodiment may include a camera 110, a storage 120, a processor 130, and a display 140.

The camera 110 is a component for obtaining a captured image by capturing an image through a lens. The camera 110 may include a camera and may be provided in a front side or a rear side of the user terminal apparatus 100. If a camera control application (e.g., a capture application, etc.) of the user terminal apparatus 100 is executed or a control input relating to capture is input on the executed application, the camera module of the camera 110 may be driven. For example, if a capture command is received from a user, the processor 130 may control the camera 110 to capture the image. At this time, the captured image may be encoded and compressed through various kinds of image processing and may be stored in the storage 120.

The storage 120 is a component for storing a food intake history of the user and may be implemented as a hard disk drive (HDD), a solid-state drive (SSD), a dynamic random access memory (DRAM), a static random access memory (SRAM), a ferroelectric random access memory (FRAM), or a flash memory. The food intake history may be information about food that the user has eaten. The food intake history may be received directly from the user or estimated by receiving the captured image from the camera 110. For example, the food intake history may include information about the types of food that the user has eaten, an intake date and time, etc. and may include an intake frequency of the user regarding a specific kind of food computed therefrom.

The storage 120 may also store each of feature values of a plurality of food types for estimating a kind of food by comparing the feature values and a feature value extracted from the captured image from the camera 110. The storage 120 may also store calorie data for each food type.

The processor 130 is a component controlling a general operation of the user terminal apparatus 100. The processor 130 may extract a food image from the captured image and estimate a kind of food included in the captured image based on feature information of the extracted food image and the stored food intake history. The feature information of a food item may be data that describe that particular item. Thus, the feature information may be used to uniquely identify a particular type of food. The feature information may include information related to, for example, color, shape, and texture of the food item.

Specifically, the processor 130 may extract at least one food image regarding a food area included in the captured image by using feature information of an image regarding a color, a shape, a texture, etc. from the captured image. At this time, the processor 130 may estimate the type of food by comparing the feature information of the extracted food image and the feature values of kinds of food stored in the storage 120. The processor 130 may perform pre-processing on the captured image for easily extracting the feature information from the captured image. For example, the processor 130 may reduce or enlarge the captured image and recognize a boundary of food from the captured image. A method of recognizing the boundary of the food may use a line Hough transform method, an image thresholding method, or a texture analysis method.

There may be a limit to the feature values stored in the user terminal apparatus 100 in terms of a size of data. Even if it is possible to store features values for every food type, the recognition rate of a food type may be low. Accordingly, the processor 130 may apply a weight to each type of food based on the food intake history, and, if food included in the captured image is determined to be consisting of a plurality of different types of food, the food may be categorized as a food type that has the highest weight among the various detected food types. The weight may be a numerical value that represents preference or bias toward a given food item over other food items For example, if the user mainly eats around 100 different kinds of food, the processor 130 may apply respective weights to the 100 food types that the user mainly eats. Thereafter, when the processor 130 detects a food type of the extracted food image from the captured image, there may be a case where, due to a similarity of feature information, the corresponding food image is detected as mushroom spaghetti, to which a weight is applied as food that the user regularly eats, or seafood spaghetti, to which no weight is applied as food having no history of the user having eaten it. In this example, the processor 130 may determine the food type included in the food image as the mushroom spaghetti because of the applied weight, thereby applying a higher detection probability to the types of food that the user eats more frequently.

The processor 130 may apply high weights in order of a high intake frequency among food types. That is, a high intake frequency of a specific kind of food means a high weight of that specific kind of food. When the user obtains a captured image of the specific kind of food, among various different kinds of food having similar feature information to that of the specific kind of food, the specific kind of food may have the highest probability of being selected for the captured image.

For example, when the processor 130 estimates the kind of the food included in the extracted food image from the captured image, there may be a case where, due to a similarity of feature information, the corresponding food image may be determined to be either soy milk, to which a weight value of 10 is applied as the food that the user regularly eats, or low fat milk, to which a weight value of 5 is applied as food having a similar but less frequent intake history. At this time, the processor 130 guesses the kind of the food included in the food image as the soy milk, to which a higher weight is applied, thereby applying a higher probability of selection to the food type having a higher user intake frequency.

The processor 130 may determine a food type in this manner and update the food intake history according to a user input or at least one of such determination results.

The display 140 is a component for displaying information. In particular, the display 140 may display relevant information about a determined food type. The display 140 may be implemented as a liquid crystal display (LCD) panel, an organic light emitting diode (OLED), a transparent display, a flexible display, etc., but is not limited thereto. The display 140 may also include a driving circuit that may be implemented as amorphous silicon thin-film transistors (a-si TFT), a low temperature polysilicon (LTPS) TFT, an organic TFT (OTFT), a backlight unit, etc.

Figure 2:
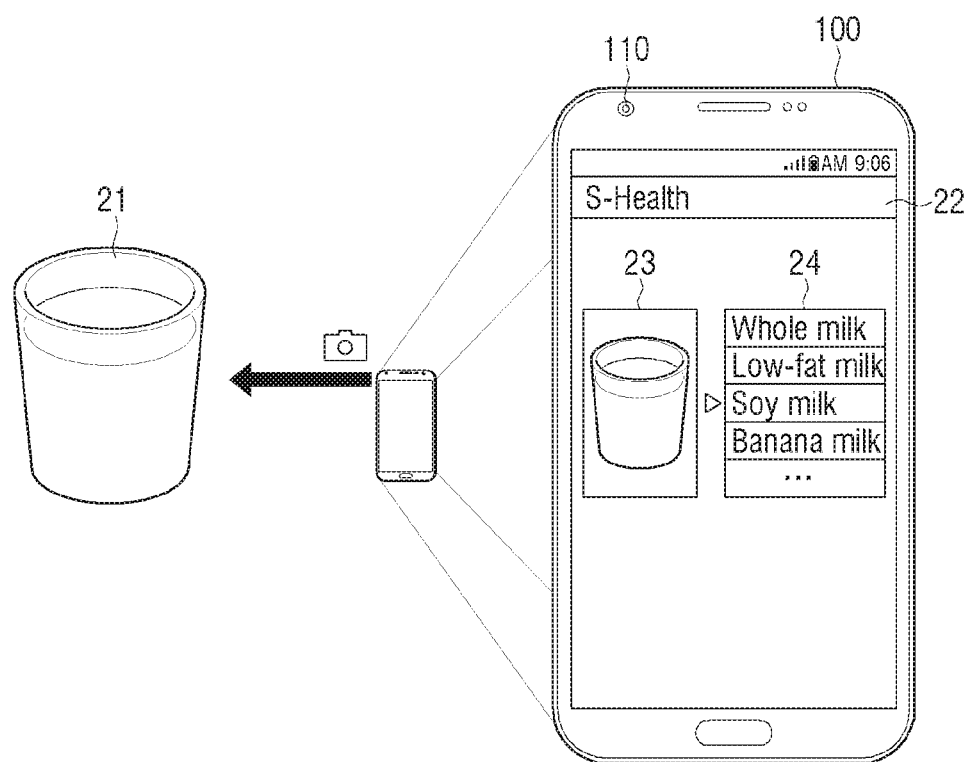
FIG. 2 is a diagram illustrating a method for determining a type of food by capturing an image of the food according to an exemplary embodiment.

FIG. 2 is a diagram illustrating a method for determining a type of food by capturing an image of the food according to an exemplary embodiment.

As shown in FIG. 2, when a captured image of soy milk 21 is obtained by capturing a glass of soy milk 21 by using the user terminal apparatus 100, the type of food captured in the image may be determined by executing a healthcare application called "S-Health" in this example. Also, the captured image may be obtained by receiving a control input relating to capturing from a user in the executed S-Health application, and the kind of the food included in the captured image may be determined.

As shown in FIG. 2, on a screen 22 in which the S-Health application is being executed, the processor 130 may compare the feature information of the type of food included in captured image 23 and feature information database of a plurality of food types stored in the storage 120, and display a list 24 of food types having similar difference is within a threshold value) feature information to the feature information of the food type included in the captured image 23. The list 24 of food types having similar feature information may include, for example, whole milk, low-fat milk, soy milk, banana milk, etc. Having similar feature information may indicate that the difference between the two values is within a threshold value.

If a user selects soy milk from the displayed list 24, the processor 130 may recognize the corresponding food as soy milk, display relevant information (e.g., calories, etc.) about soy milk, and store information indicating a soy milk intake in the storage 120. The processor 130 may also apply a weight to soy milk selected by the user in the list 24 of food types having similar feature information to the feature information of the food type included in the captured image 23. Thereafter, if such a process is repeated for a preset number of times, when the user obtains a captured image of soy milk, the processor 130 may be more likely to determine the food item as soy milk and display relevant information about soy milk. This will be described in detail with reference to FIG. 3.

FIG. 3 is a diagram illustrating a method for applying weights to food types according to an exemplary embodiment. As shown in FIG. 3, a table in which a weight is applied to each of various kinds of milk sharing similar feature information may be stored. The weight may influence the likelihood of selection for the type of food the weight is being applied to. In other words, the higher the weight is applied, the more likely the apparatus will select the given food item among multiple food types with similar feature information.

In particular, as a process in which a user selects soy milk from the list 24 of food types having similar feature information to feature information of soy milk is repeated, the weight of soy milk may be cumulatively increased. In this example, soy milk having the highest user intake frequency, and therefore the highest cumulative weight value of 10, corresponds to a food type having the highest probability of selection for the type of food captured in the image among various kinds of milk that share similar feature information. In this example, a weight applied to each type of food is reduced in order of whole milk, low-fat milk, and banana milk, which coincides with the order of intake frequency. Strawberry milk has a weight value of "0" and corresponds to a kind of food that the user does not eat.

However, a weight may be a value that may be relatively adjusted between a food type having a higher intake frequency and a food type having a lower intake frequency among various kinds of food sharing similar feature information.

Figure 4:
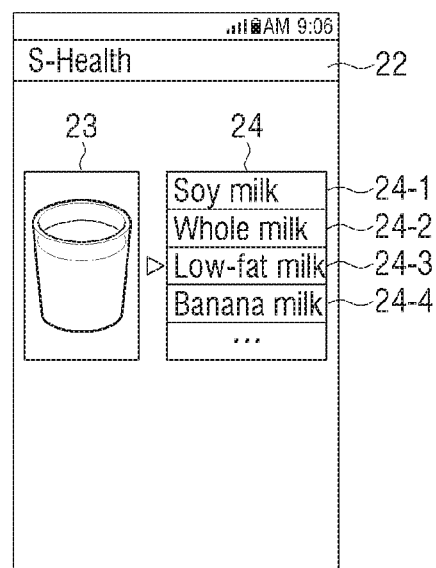
FIG. 4 is a diagram illustrating a method for determining a food type having a high weight according to an exemplary embodiment.

FIG. 4 is a diagram illustrating a method for determining a food type having a high weight according to an exemplary embodiment.

As shown in FIG. 4, the list 24 of food types having similar feature information may be displayed in order of the amount of weight applied to different food types. That is, unlike the embodiment described with reference to FIG. 2, the processor 130 may display the list 24 in which soy milk 24-1 with the highest weight is arranged at the top and whole milk 24-2, low-fat milk 24-3, and banana milk 24-4, etc. are arranged below the soy milk 24-1 in the descending order of their weights. A user may select soy milk 24-1 arranged at the top of the list 24 to induce a food image 23 to be recognized as soy milk 24-1. However, when a kind of food included in a captured image is not soy milk, the user may select an appropriate food type from the list 24.

FIGS. 5A through 5D are diagrams for illustrating a method for updating a food type beyond a recognition range according to an exemplary embodiment.

Figure 5A:
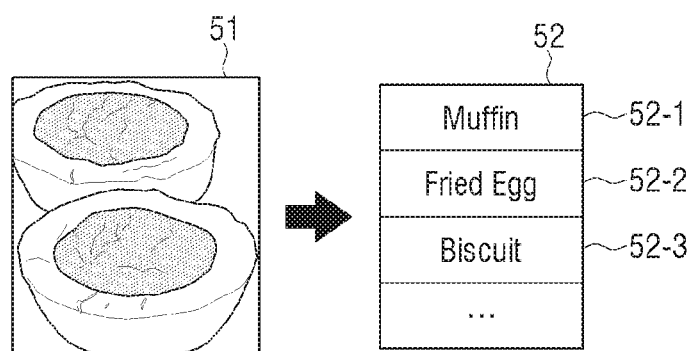
FIGS. 5A through 5D are diagrams illustrating a method for updating a food type beyond a recognition range according to an exemplary embodiment.

FIG. 5A illustrates a captured image 51 of an egg tart that a user is to eat and a detection result thereof. As shown in FIG. 5A, as a recognition result based on feature information extracted from the captured image 51 of the egg tart, a list 52 that includes a muffin 52-1, a fried egg 52-2, and a biscuit 52-3 may be displayed. In this case, because the list 52 does not include an egg tart, the user cannot select an egg tart, and thus it is necessary to manually input the appropriate food type.

Figure 5B:
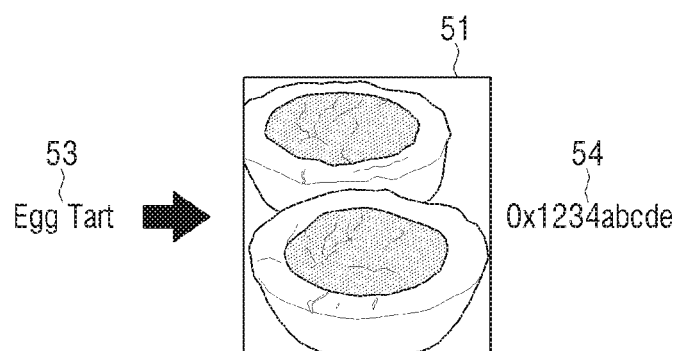

As shown in FIG. 5B, the user may update the stored table by manually inputting "egg tart" 53 as the new food type and associating the manually input "egg tart" 53 with feature information 54 extracted from the captured image 51. That is, the processor 130 may dynamically update a food intake history stored in the storage 120 based on matching information of a captured image and a food type manually input by the user. Also, information matched by the user may be additionally stored in food feature information of a food recognition model 240 of a server 200, and a food intake history of a user database 250, as will be described in greater detail with reference to FIG. 12. The processor 130 may further include "egg tart" in the storage as a food type having similar feature information to the extracted feature information 54, along with muffin 52-1, fried egg 52-2, and biscuit 52-3. At this time, the processor 1350 may apply a weight to "egg tart" directly input by the user.

Figure 5C:
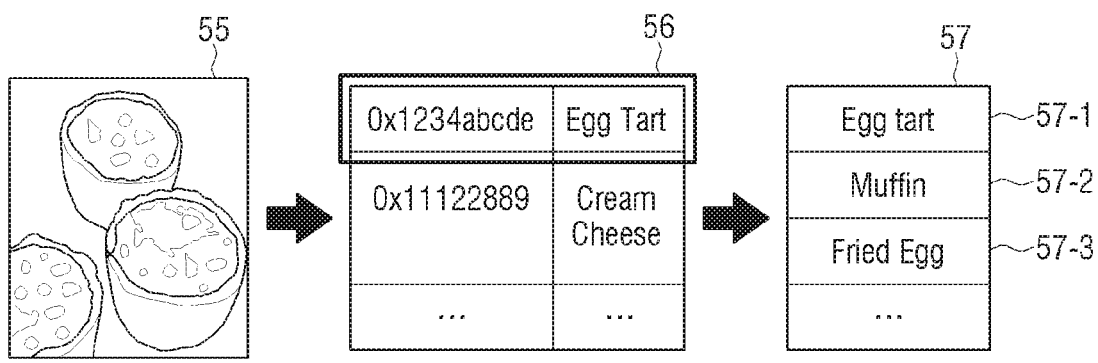

FIG. 5C is a diagram illustrating a method of detecting a food type from a captured image of an egg tart when a user eats an egg tart for the second time after the egg tart was manually input. As shown in FIG. 5C, in order to estimate a kind of food having similar feature information to feature information of an egg tart extracted from a captured image 55, the processor 130 may extract information 56 in which the feature information and the egg tart are matched and stored in a matching table based on a manual input of a user, and display a list 57 in which an egg tart 57-1 with a higher weight is at the top and a muffin 57-2 and a fried egg 57-3 are placed toward the bottom. At this time, the user may select the egg tart from the displayed list 57 to induce the food included in the captured image 55 to be recognized as an egg tart. The processor 130 may additionally apply a weight to the recognized egg tart and store intake information of the egg tart as an intake history.

Figure 5D:
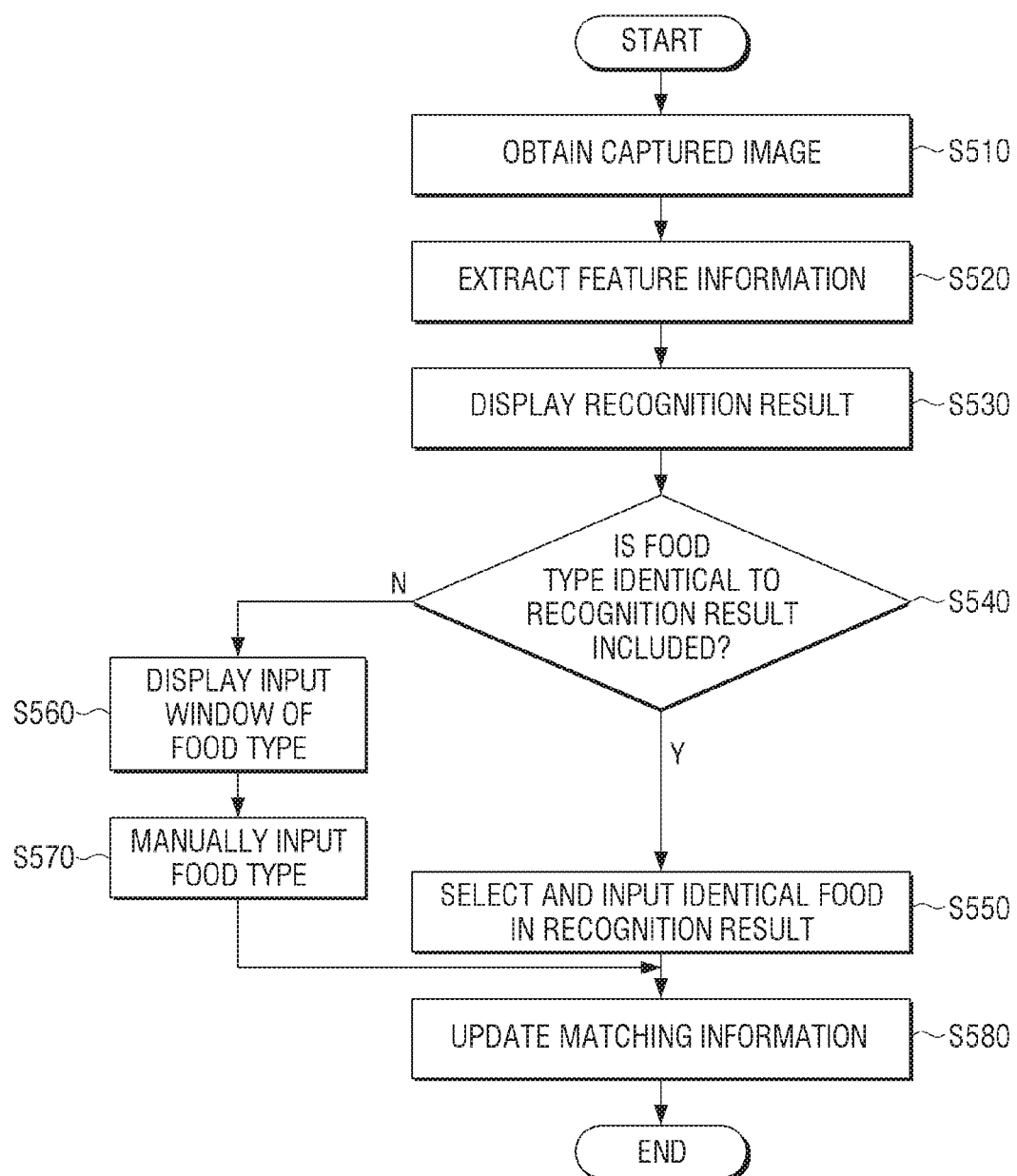

FIG. 5D is a flowchart for describing a method of updating a food type beyond a recognition range according to an exemplary embodiment.

As shown in FIG. 5D, the user terminal apparatus 100 may obtain a captured image of food (S510). The captured image of food may be obtained by capturing a photo through a camera while a healthcare application is executed. Also, the captured image may be an image that is previously stored in a user terminal apparatus 100. At this time, the healthcare application may interact with a photo application that may upload a previously stored image.

Thereafter, the user terminal apparatus 100 may extract feature information from the obtained captured image and recognize or detect the food type by using previously stored intake history information of a user (S520). At this time, the user terminal apparatus 100 may detect the type of food by comparing feature information of the food based on the food model database stored in the storage 120 or the server.

If the type of food is recognized, the user terminal apparatus 100 may display a recognition result (S530). At this time, the recognition result may be displayed in the form of a list of food types having similar feature information. When a kind of food identical to the recognition result is included (S540:Y), the user may perform an input by selecting food identical to the food included in the captured image from the recognition result (S550).

When the type of food identical to the recognition result is not included (S540:N), the user terminal apparatus 100 may display an input window by which a type of food may be directly typed and input (S560). The user may perform an input by manually typing in the food type (S570).

If the input is complete, the user terminal apparatus 100 may update a food intake history by matching the feature information of the food included in the captured image and information about a food type selected by the user (S580).

Figure 6:
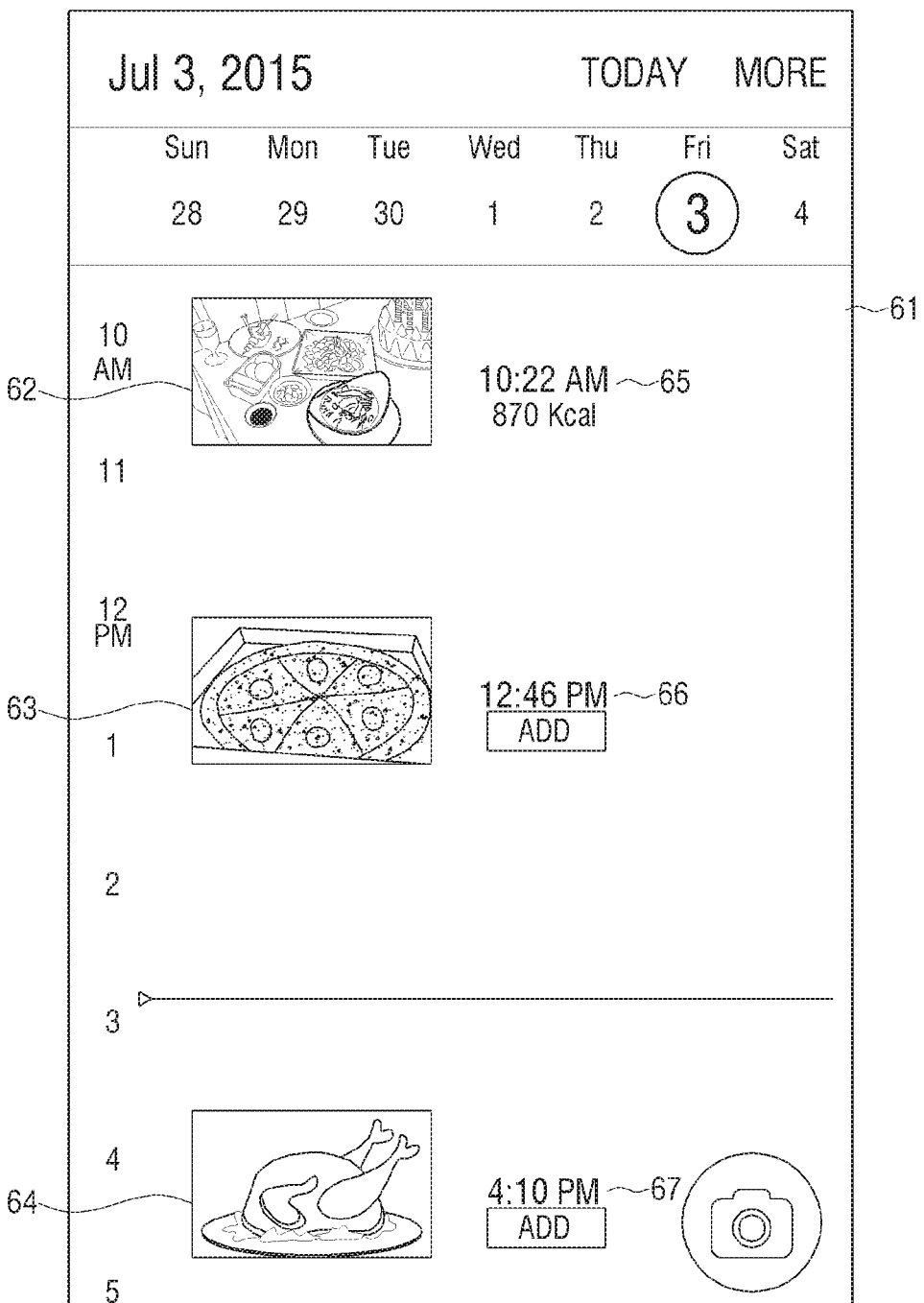
FIG. 6 is a diagram illustrating a user interface (UI) that displays a captured image in a timeline form according to an exemplary embodiment.

FIG. 6 is a diagram illustrating a user interface (UI) that displays a captured image in a timeline form according to an exemplary embodiment.

The processor 130 may store captured images in the storage 120, and if a preset event occurs, select captured images including the food image from the captured images stored in the storage 120, and display a UI in a timeline in which the selected captured images are aligned and displayed in order of capturing time on the display 140.

In this regard, the preset event may include an event in which a healthcare application is executed or an event that obtains a captured image while the healthcare application is executed as a background in the user terminal apparatus 100. Specifically, if an image of food that a user eats is captured for each meal, the processor 130 may store the captured image. Thereafter, when the user executes the healthcare application, the processor 130 may select a captured image including the food image by using feature information such as a color, a texture, a shape, etc. of the food from the captured images stored in the storage 120 (first filtering). As shown in FIG. 6, the processor 130 may display the UI in the timeline provided by the healthcare application and align and display captured images including the food image selected on the corresponding UI capturing time sequentially. At this time, images aligned and displayed in order of capturing time may be at least one food image extracted from a captured image.

As shown in FIG. 6, the processor 130 may extract information about a capturing date and time from metadata (e.g., exchangeable image file format (EXIF) information) included in the captured image and display the corresponding captured image and relevant information such as calorie information in an area corresponding to the extracted information about the capturing date and time on the UI in which information may be input for date and time by using the extracted information.

Figure 7:
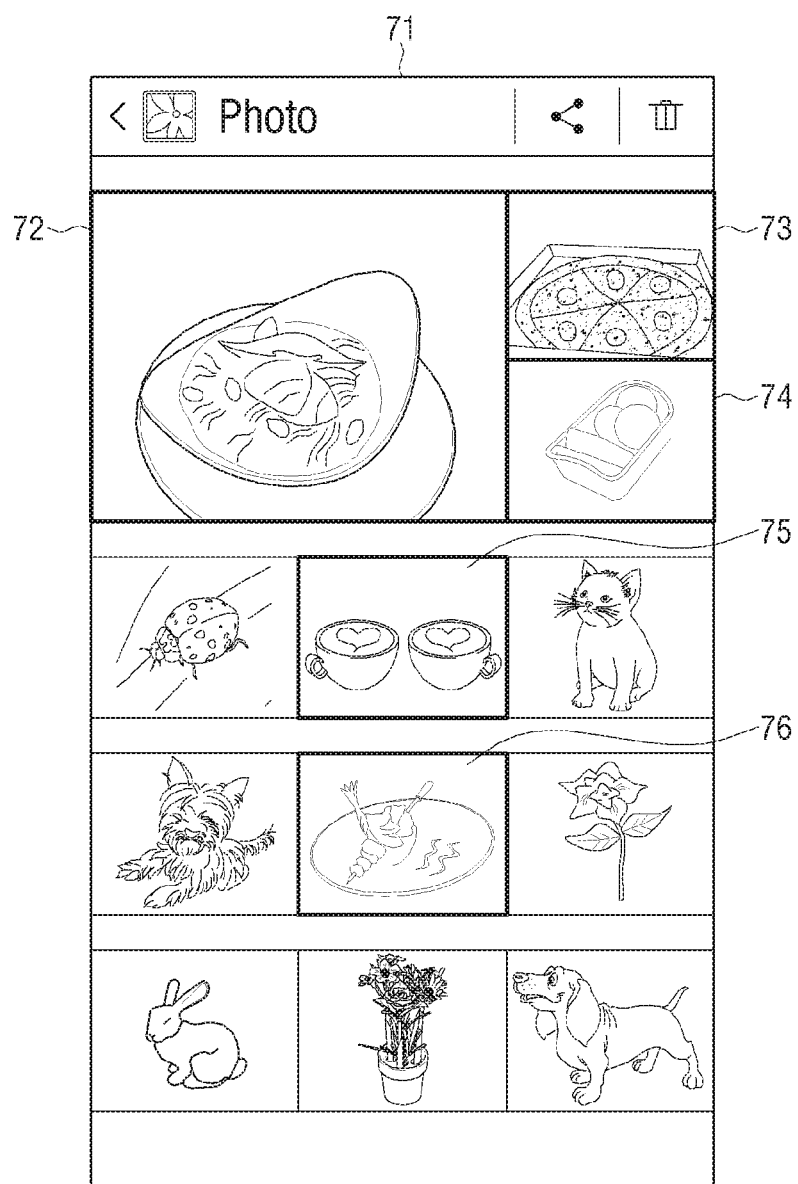
FIG. 7 is a diagram illustrating a method for selecting a captured image including a food image among stored captured images according to an exemplary embodiment.

For example, food that the user is about to eat as breakfast at 10:22 AM is captured, food that the user is planning to eat for lunch at 12:46 PM is captured, and food that the user is planning to eat as snack at 4:10 PM is captured. Also, it is assumed that, in addition to the food that the user has eaten, various landscape photos are also captured during outdoor activities. At this time, information about each capturing time may be included in each captured image as metadata and stored. Thereafter, when the user executes the healthcare application before retiring to bed, the processor 130 may select only images including food items from the captured images stored in the storage 120. At this time, as the images including food, only an image 62 captured at breakfast time, an image 63 captured at lunch time, and an image 64 captured at snack time may be selected. The landscape photos captured during outdoor activities do not include food and thus may be excluded. For example, as shown in FIG. 7, the processor 130 may interact with a photo album application 71 that stores captured images and select and classify one or more captured images 72 through 76 that include food from among the images stored and managed by the photo album application 71.

The processor 130 may align and display each captured image on areas corresponding to capturing dates and time of captured images 62 through 64 on a UI 61 in a timeline by using metadata included in the classified captured images 62 through 64. The processor 130 may detect a food type included in each captured image by using feature information of a food image extracted from each captured image and a food intake history stored in the storage 120 and display relevant information such as calorie information about the detected food item.

As a different exemplary embodiment, the healthcare application may be always executed in the background in the user terminal apparatus 100. Whenever the user captures an image, the first filtering that selects only images including food from captured images may be performed. Also, the images selected through the first filtering may be aligned and stored in areas corresponding to each capturing date and time in real time on the UI 61 in a timeline.

That is, irrespective of a time when the user executes the healthcare application, the processor 130 may generate a UI in a timeline in which captured images are automatically aligned for date and time.

Figure 8:
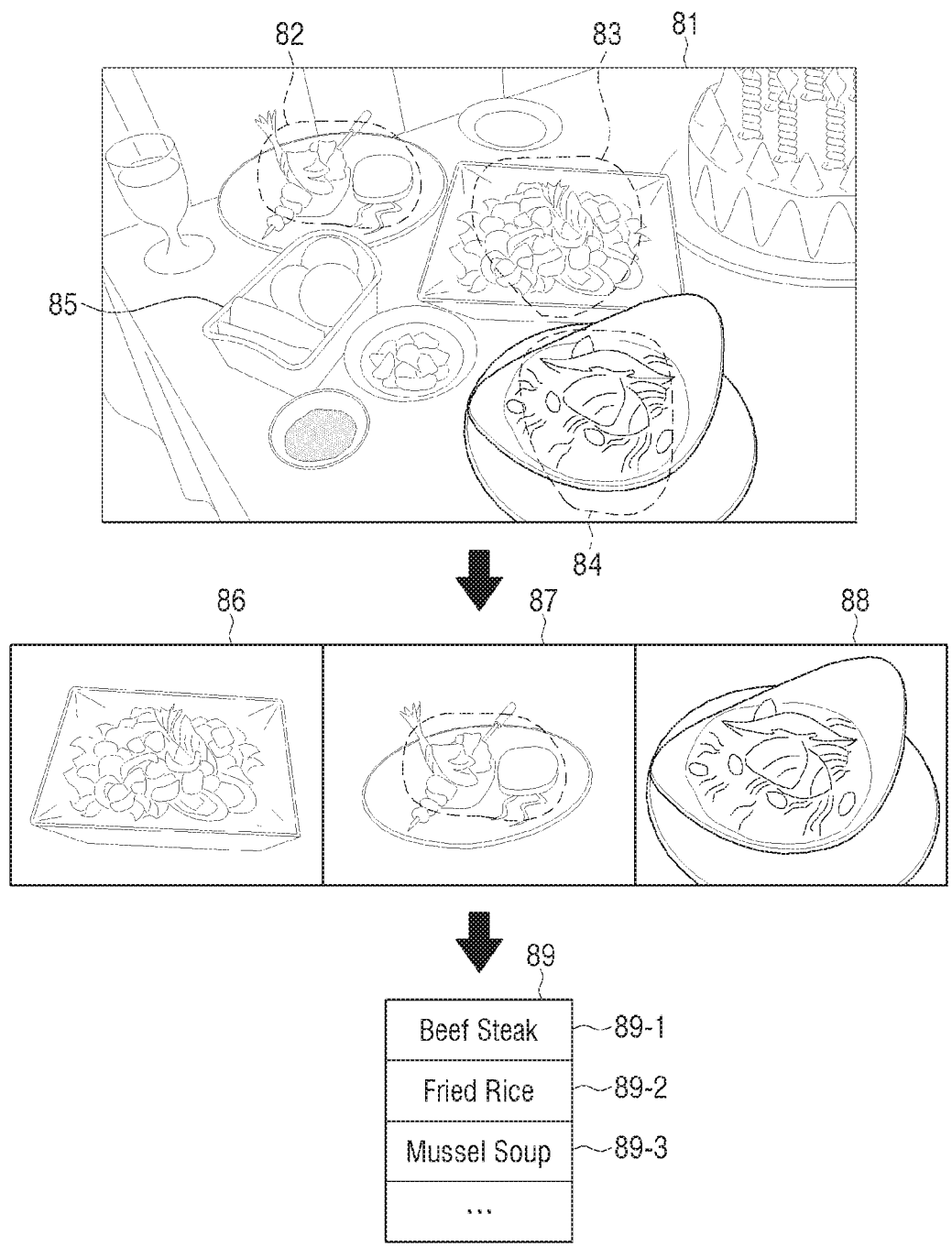
FIG. 8 is a diagram illustrating a method for detecting a food type only selected by a user according to an exemplary embodiment.

FIG. 8 is a diagram illustrating a method for detecting a food type only selected by a user according to an exemplary embodiment.

As shown in FIG. 8, a plurality of food items may be included in a captured image 81 obtained from the camera 110. The processor 130 may extract feature information about each of the plurality of food items included in the captured image 81 and detect corresponding food types.

However, the captured image 81 obtained from the camera 110 may also include food that the user does not eat. Such a situation may frequently take place when the user is sharing a meal with other people or on a buffet table. Thus, it is necessary to exclude food that the user does not eat in a food intake history and only display relevant information about the types of food that the user has eaten.

FIG. 8 illustrates a UI screen for selecting only those food items that the user actually has eaten from among a plurality of food items included in the captured image 81. When the user selects an area of the captured image 81 in which a food item is displayed on the healthcare application, the processor 130 may detect main saliencies 82 through 84 of food items as shown in FIG. 8 based on the areas selected by the user, and respectively generate cropped images 86 through 88 (second filtering). Also, the selection areas of the user may be an area drawn and designated by the user on the captured image 81.

The processor 130 may detect a food type from feature information of a food image included in each of the images 86 through 88 by a machine learning-based recognition system. The machine learning-based recognition system is referred to as a learning system using an artificial intelligence technology combined with unsupervised learning, which is more active than the conventional supervised learning, which requires intervention of a human capable of monitoring the self learning of a computer. Specifically, the processor 130 may extract feature information of each of the detected images 86 through 88, and may sequentially input the extracted feature information of each of the images 86 through 88 in an input layer of machine learning algorithm with respect to food recognition, and may derive a recognition result of each of the images 86 through 88. The processor 130 may guess a kind of food included in each of the images 86 through 88 from the derived recognition result. The processor 130 may sum and store a result of the estimated food type as a list 89 including estimated food types 89-1 through 89-3. The stored estimation result may be used as information for providing relevant information about the estimated food type.

The processor 130 may allow an automatic classifier to learn a kind of food having a feature information value obtained from the food image. The automatic classifier may use an algorithm based on a machine learning technique such as Bayesian classifier, support vector machine (SVM), or an artificial neural network (ANN), etc. Each automatic classifier may make an automatic classification structure by using the feature value extracted from the food image by using an intrinsic principle. The processor 130 may generate an automatic classifier capable of classifying food types and perform learning on various types of food, and accordingly, making it possible to evaluate a type of food included in each food image with respect to a plurality of food images. The processor 130 may even detect an amount of food present by using the automatic classifier, and thus achieving a more accurate estimation.

Figure 9:
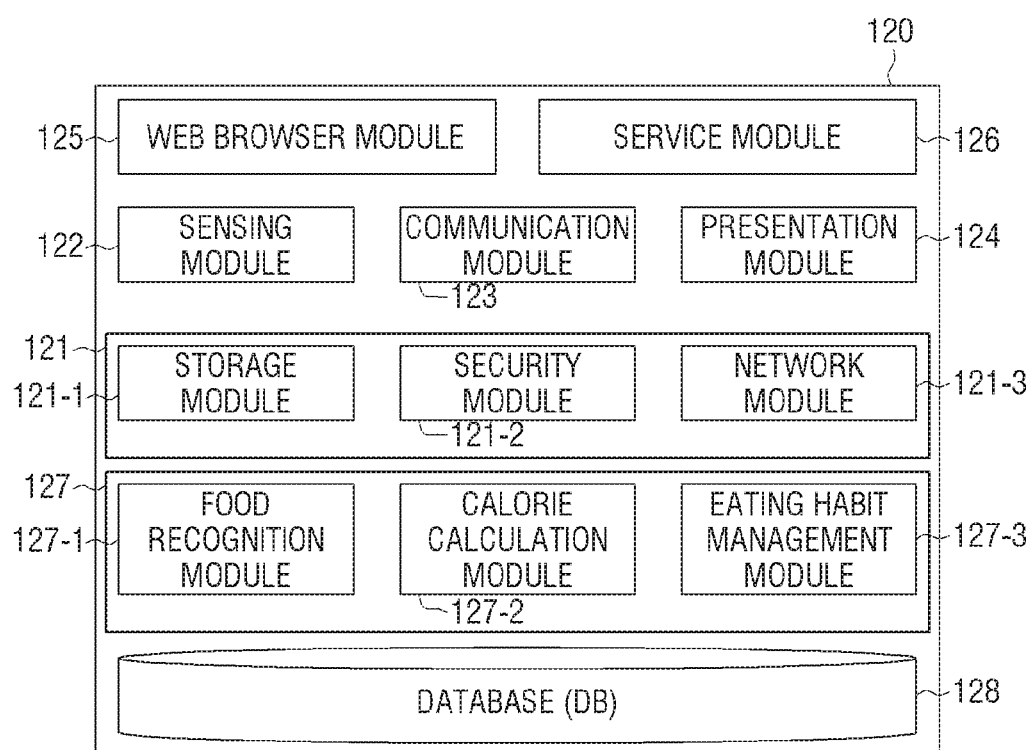
FIG. 9 is a detailed block diagram illustrating a configuration of a storage of a user terminal apparatus according to another exemplary embodiment.

FIG. 9 is a detailed block diagram illustrating a configuration of the storage 120 of the user terminal apparatus 100 according to another exemplary embodiment.

As shown in FIG. 9, the storage 120 may include a base module 121, a sensing module 122, a communication module 123, a presentation module 124, a web browser module 125, a service module 126, a diet management module 127, and a database (DB) 128 storing a food recognition model. Each of the modules shown in FIG. 9 and other figures may be implemented by software, hardware, or a combination of both. For example, a module may be implemented as instructions stored in a non-transitory computer-readable storage medium, the instructions causing one or more hardware components, such as a processor, to perform various operations disclosed herein.

The base module 121 may process a signal transferred from various hardware components included in the user terminal apparatus 100 and transfer the signal to an upper layer module. A storage module 121-1 is a program module managing the DB 128 or a registry. A security module 121-2 is a program module supporting certification on hardware, request permission, secure storage, etc. A network module 121-3 is a module for supporting a network connection.

The sensing module 122 is a module collecting information from various sensors, analyzing and managing the collected information.

The communication module 123 is a module for communicating with external devices. The communication module 123 may include a messaging module and a phone module.

The presentation module 124 is a module for configuring a display screen. The presentation module 124 includes a multimedia module for reproducing and outputting multimedia contents and a UI rendering module performing GUI and graphics processing.

The web browser module 125 is a module for performing web browsing by accessing web servers and rendering web pages.

The service module 126 is a module including various applications for providing various services. Specifically, the service module 126 may include various program modules such as a social media program, a content reproduction program, etc.

The diet management module 127 is a module for providing and managing diet-related information about a user analyzed from a captured image on a healthcare application. The diet management module 127 includes a food recognition module 127-1, a calorie calculation module 127-2, and an eating habit management module 127-3.

The food recognition module 127-1 may extract feature information from a captured image through machine learning regarding a type and an amount of food and detect or recognize the type and the amount of food from the extracted feature information. In this regard, the amount of food may be information input from a user through the user terminal apparatus 100. The food recognition module 127-1 may include a pre-processing unit performing pre-processing on a received captured image, an image splitting unit separating a food area of the pre-processed food image, and a feature extraction unit extracting feature information of the separated food area (i.e., a region of the image that contains a food item). The feature extracting unit extracts feature information about colors, shapes, textures, etc., with respect to the separated food area.

The calorie calculation module 127-2 may calculate calories of food based on the detected food type and the amount of food from the food estimation module 127-1. Calories according to the type of food may be obtained by using calorie data stored in the database 128.

The eating habit management module 127-3 is a module for guiding and managing an eating habit of a user by using food types, amounts, and calories of food that the user has partaken. The eating habit management module 127-3 may be modified by a manager such that various functions are provided in accordance with the purpose of use. For example, the eating habit management module 127-3 may determine the types of food that the user prefers, analyze an intake state, and inform the user of any nutrients that the user may be lacking.

The database 128 may store various recognition models necessary for food recognition. The user terminal apparatus 100 may compare a captured image and the recognition models stored in the database 128, and determine the food type. The database 128 may store calorie data of various types of food. The stored calorie data may be used for the calorie calculation module 127-2 to calculate calories according to the respective types of food.

Figure 10:
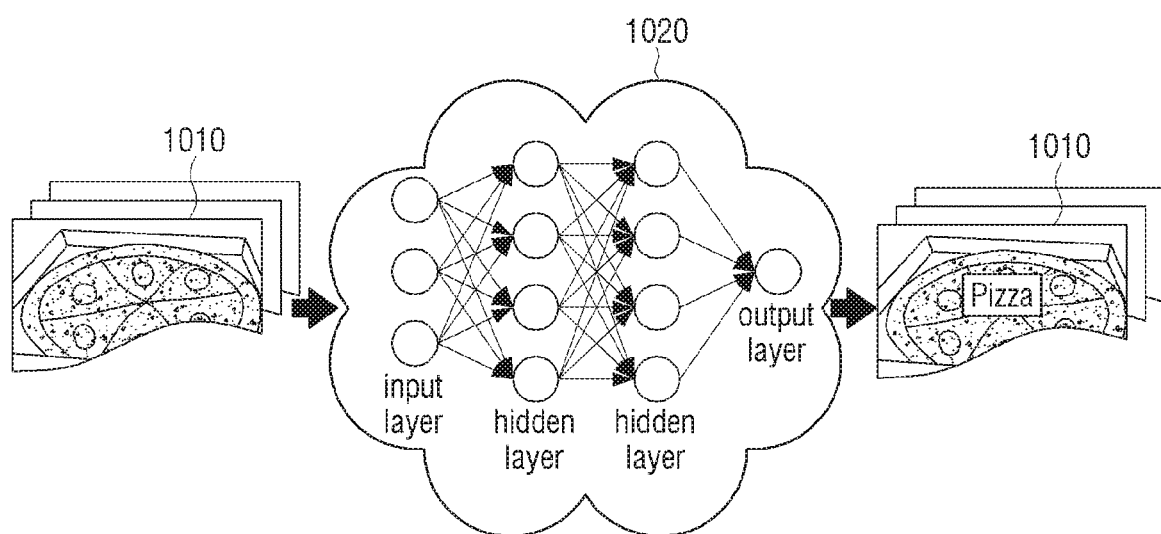
FIG. 10 is a diagram illustrating a food recognition process based on a machine learning technique according to an exemplary embodiment.

FIG. 10 is a diagram illustrating a food recognition process based on a machine learning technique according to an exemplary embodiment.

Food type recognition of the present disclosure may be performed by a machine learning-based recognition system. In the present disclosure, a deep learning-based recognition system is, by way of example, described as a classification system by a series of neural network-based machine learning algorithm.

The deep learning-based recognition system may include at least one classifier 1020. The classifier 1020 may correspond to one processor or a plurality of processors. A processor may be implemented as an array of multiple logic gates or as a combination of a general-purpose microprocessor and a memory storing a program that may be executed in the general-purpose microprocessor. The classifier 1020 may be implemented as a neural network-based classifier, SVM (Support Vector Machine), an adaboost classifier, a Bayesian classifier, a perceptron classifier, etc. An embodiment that the classifier 1020 of the present disclosure is implemented as a convolutional neural network (CNN)-based classifier is described below. The neural network-based classifier is an arithmetic operation model implemented to model a calculation capability of a biological system by using many artificial neurons connected by connection lines and performs a human recognition action or a learning process through connection lines having a connection intensity (weight). However, the classifier 1020 of the present disclosure is not limited thereto and may be implemented as various classifiers described above.

A general neural network includes an input layer, a hidden layer, and an output layer. The hidden layer may include one or more layers as necessary. A back propagation algorithm may be used as algorithm for learning the neural network.

If data is input to the input layer of the neural network, the classifier 1020 may allow the neural network to learn the neural network such that output data with respect to the input learning data is output to the output layer of the neural network. If feature information extracted from a captured image 1010 is input, the classifier 1020 may classify a pattern of the feature information into one of various classes by using the neural network and output the classification result 1010.

Figure 11:
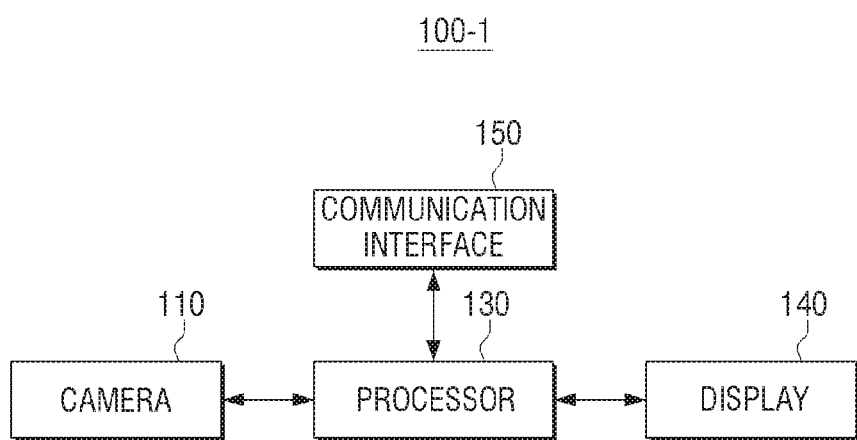
FIG. 11 is a schematic block diagram illustrating a configuration of a user terminal apparatus according to another exemplary embodiment.

FIG. 11 is a schematic block diagram illustrating a configuration of a user terminal apparatus 100-1 according to another exemplary embodiment. The user terminal apparatus 100-1 of FIG. 11 may further include a communication interface 150, instead of the storage 120.

The communication interface 150 is a component for communicating with an external server 200. The external server 200 may be a server that includes a user DB storing a food intake history of a user.

The processor 130 may transmit feature information of a food image extracted from a captured image to the external server 200. The external server 200 may determine a food type based on the extracted feature information and the food intake history, and transmit relevant information about the determined food type to the user terminal apparatus 100-1. The processor 130 may display the relevant information received from the external server 200.

That is, the food intake history of the user may be individually managed by being included in the user DB of the external server 200 for each user.

The communication interface 150 may communicate with the external server 200 according to various types of communication methods. The communication interface 150 may communicate with the external server 200 through various communication methods using radio frequency (RF) such as Bluetooth (BT), Wi-Fi, Zigbee, near-field communication (NFC), infrared (IR), etc. To this end, a communication device including a Zigbee communication device, a BT communication device, and/or a Wi-Fi communication device may be provided. A process of communicating with the external server 200 will be described in detail with reference to FIG. 12.

Figure 12:
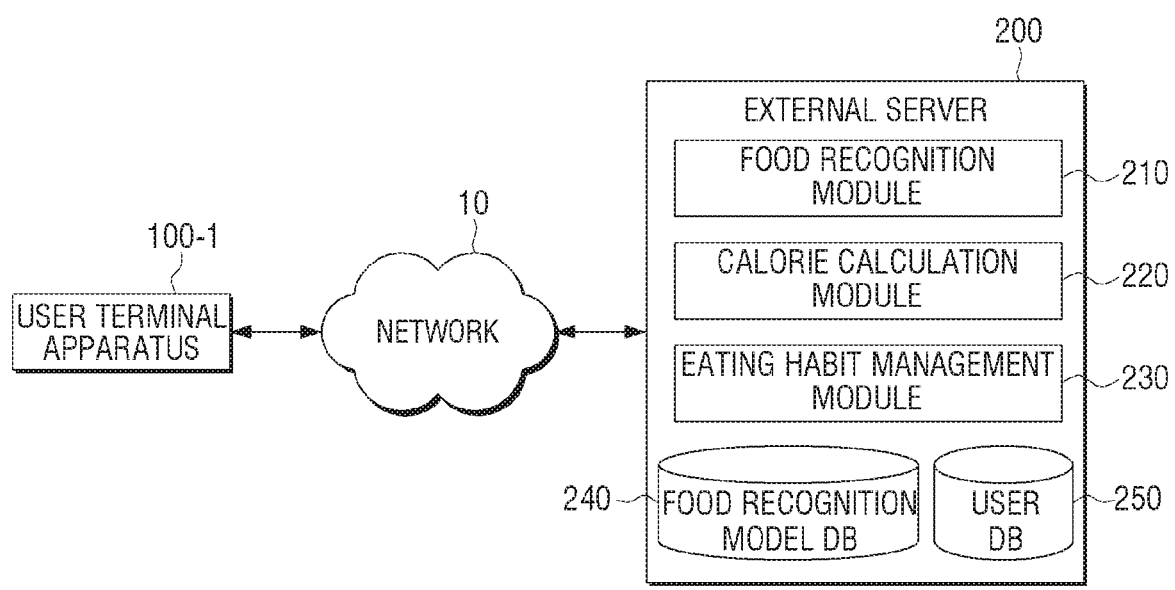
FIG. 12 is a block diagram illustrating a method for estimating a kind of food by communicating with an external server including a user database (DB) according to an exemplary embodiment.

FIG. 12 is a block diagram illustrating a method for determining a food type by communicating with the external server 200 that includes a user database (DB) according to an exemplary embodiment.

The user terminal apparatus 100-1 may enable wired or wireless communication with the external server 200 over a network 10. The network 10 may include a local area network (LAN) and/or a wide area network (WAN) such as the Internet. In particular, the communication interface 150 may communicate with the external server 200 to receive relevant information about captured food item from the user terminal apparatus 100-1 from the external server 200. Specifically, the processor 130 may extract a food image from an image captured by using the camera 110 and transmit feature information of the extracted food image to the external server 200. The processor 130 may also transmit the image itself captured through the camera 110 to the external server 200 or transmit the food image extracted from the captured image to the external server 200. At this time, the external server 200 may receive the feature information of the extracted food image, determine a type of the corresponding food by using the received feature information and/or a previously stored food intake history, and transmit the determination result to the user terminal apparatus 100-1. As another embodiment different from this, the external server 200 may receive the captured image itself, extract a food image from the received captured image, and determine a type of food included in the food image based on feature information of the extracted food image and/or the previously stored food intake history.

The external server 200 may include a food recognition module 210, a calorie calculation module 220, an eating habit management module 230, the food recognition model (DB) 240, and the user DB 250. Detailed descriptions of the food recognition module 210, the eating habit management module 230, and the food recognition model (DB) 240 are redundant as described with reference to FIG. 9, and thus are omitted.

The user DB 250 is a database storing information about a plurality of users. The user DB 250 may store food intake histories of the plurality of users.

The external server 200 may solely detect a type of food included in a captured image and generate relevant information about the detected food type. As long as a user transmits a captured image captured by using the user terminal apparatus 100-1 to the external server 200, the user terminal apparatus 100-1 may receive the relevant information about the detected food type from the external server 200 and display the information on an application.

The external server 200 may receive the captured image from the user terminal apparatus 100-1, extract a food image from the received captured image, and detect a type of food included in the captured image based on feature information of the extracted food image and/or the stored food intake history in the external server 200. The external server 200 may transmit relevant information about the detected food type to the user terminal apparatus 100-1.

That is, in the present disclosure, as shown in FIGS. 1 through 10, the user terminal apparatus 100 or the user terminal apparatus 100-1 may extract a food image from a captured image and display related information about the determined food type based on feature information of the extracted food image and/or a food intake history of a user stored in the storage 120, and additionally, as shown in FIGS. 11 and 12, communicate with the external server 200 through the communication interface 150, transmit the captured image to the external server 200, and receive and display the relevant information about the detected food type from the external server 200. The food intake history of the user may be stored in the storage 120 of the user terminal apparatus 100 or may be stored and managed by creating a corresponding user account in the external server 200.

Figure 13:
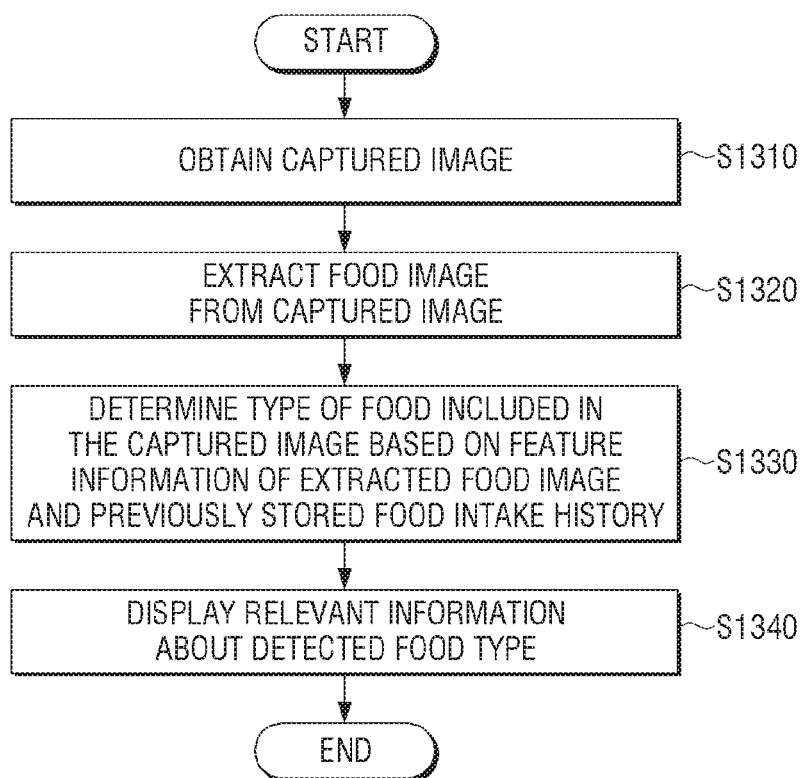
FIG. 13 is a flowchart illustrating a control method of a user terminal apparatus according to an exemplary embodiment.
Figure 15:
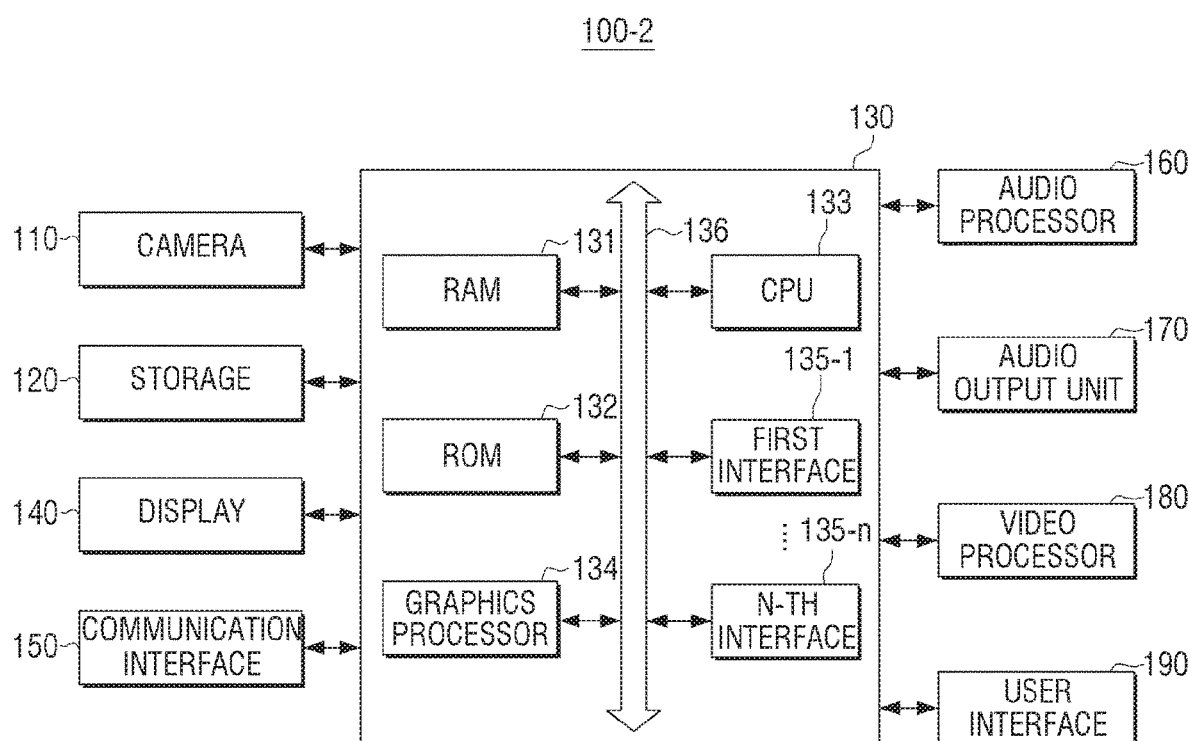
FIG. 15 is a detailed block diagram illustrating a configuration of a user terminal apparatus according to another exemplary embodiment.

FIG. 13 is a flowchart illustrating a control method of the user terminal apparatus 100 according to an exemplary embodiment. For the sake of clarity, the method is described in terms of the exemplary user terminal apparatus 100 as shown in FIG. 1 configured to practice the method. However, the exemplary user terminal apparatus 100-1 as shown in FIG. 11 or the exemplary user terminal apparatus 100-2 as shown in FIG. 15 may also perform any of the steps disclosed herein. The steps outlined herein are exemplary and can be implemented in any combination thereof, including combinations that exclude, add, or modify certain steps.

A captured image is obtained (S1310). At this time, the captured image may be obtained by receiving a control input relating to capturing from a user in healthcare application. The captured image may be a captured image previously stored in the user terminal apparatus 100 and may also be obtained by being loaded in the healthcare application. The healthcare application may interact with a photo application capable of loading a previously stored image.

Thereafter, a food image is extracted from the captured image (S1320). The user terminal apparatus 100 may automatically extract the food image by a classification system by a machine learning technique based on feature information of the captured image. The food image may also be manually extracted by the user. Specifically, when the user selects an area displaying food on the captured image displayed on the healthcare application, the user terminal apparatus 100 may detect a main saliency of the food based on a selected area of the user and generate the food image. The user may select the area by drawing or tracing an outline of the area on the captured image.

Thereafter, a type of food included in the captured image is determined based on the feature information of the extracted food image and/or a previously stored food intake history (S1330). A weight may be applied for each type of food based on the previously stored food intake history. Specifically, if it is determined that the captured image contains a plurality of different food types, a food type having the highest weight among the different food types may be selected at the most likely food type for the image. The food intake history may include types of food that the user has eaten and an intake frequency related to each food type. The weight may be applied to each of the food types according to a respective intake frequency.

A list, from which one of the food type candidates is selected based on the feature information of the extracted food, may be displayed in the order of the weights assigned to the food types. If a specific kind of food is selected from the list according to a user input, the extracted food image may be recognized as the selected food type.

If a plurality of food images are extracted from the captured image, a UI for selecting at least one of the extracted food images may be provided, and a food type of the selected food image may be determined through the UI.

Thereafter, relevant information about the detected food tpe is displayed (S1340). Specifically, captured images may be stored, if a preset event occurs, captured images including a food image is selected from the stored captured images, and the selected captured images may be aligned in order of a capturing time and may be displayed on a UI in a timeline. The relevant information about the type of food may include the food type and/or calorie information.

Also, the amount of calories that a user has eaten may be calculated from the amount of food included in the captured image input from the user and displayed. The input amount of food may be stored as information for determining an amount of food of the same kind.

Also, the food intake history may be updated according to a user input and/or an food recognition result.

Figure 14:
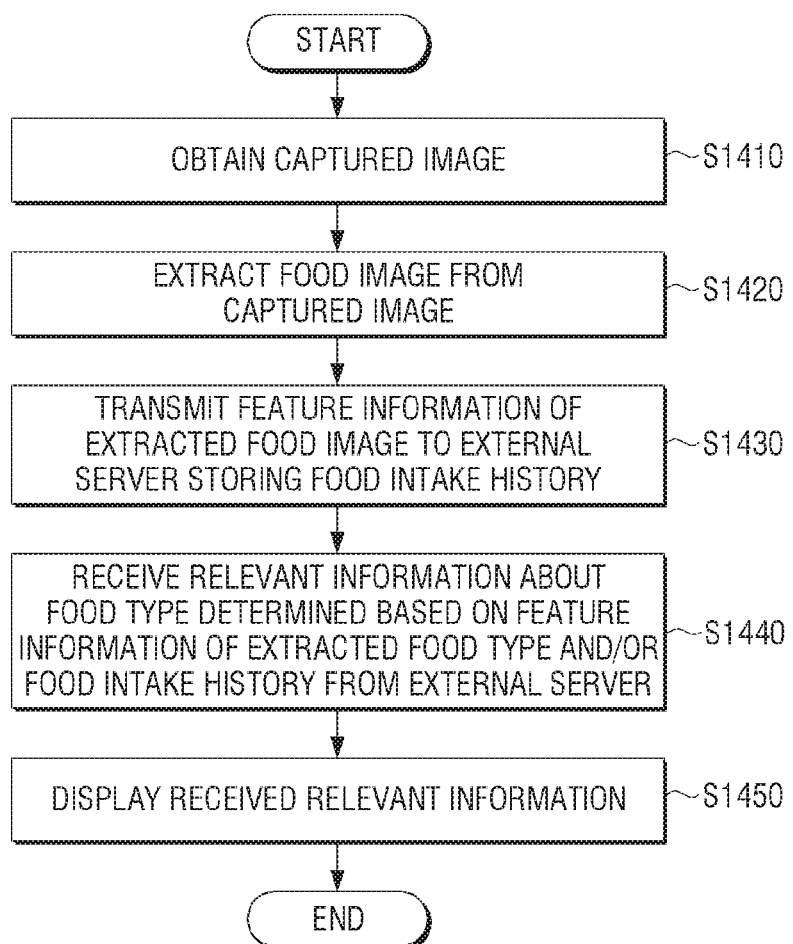
FIG. 14 is a flowchart illustrating a control method of a user terminal apparatus according to another exemplary embodiment.

FIG. 14 is a flowchart illustrating a control method of a user terminal apparatus according to another exemplary embodiment.

Firstly, a captured image is obtained (S1410), and a food image is extracted from the obtained captured image (S1420). Detailed descriptions in this regard are the same as described with reference to FIG. 13. Thereafter, feature information of the extracted food image is transmitted to an external server storing a food intake history (S1430).

Thereafter, relevant information about the food type determined based on the feature information of the extracted food type and/or the food intake history is received from the external server (S1440). The external server may compare feature information of food by using a stored food model DB when determining the food type. The external server 200 may preferentially recognize a food type to which a higher weight is applied based on intake history information of a user stored in a user DB by additionally using the user DB. Also, when the user terminal apparatus receives food types corresponding to captured images as many as a preset number of times from the user and stores the food types as intake history information, the food types may be detected by using only the user DB.

Thereafter, the user terminal apparatus displays the received relevant information (S1450).

FIG. 15 is a detailed block diagram illustrating a configuration of a user terminal apparatus 100-2 according to another exemplary embodiment.

As shown in FIG. 15, the user terminal apparatus 100-2 according to another exemplary embodiment may include the camera 110, the storage 120, the processor 130, the display 140, the communication interface 150, an audio processor 160, an audio output unit 170, a video processor 180, and a user interface 190. Descriptions of redundant configurations as configurations described with reference to FIGS. 1 through 9 are omitted below. Each of the modules, units, and components represented in FIG. 15 and other figures may be implemented by software, hardware, or a combination thereof.

The storage 120 is a component for storing a food intake history of a user and storing various modules for driving the user terminal apparatus 100-2.

Specifically, the storage 120 may include a base module processing a signal transferred from each hardware component included in the user terminal apparatus 100-2, a storage module managing a DB or a registry, a security module, a communication module, a graphics processing module, an audio processing module, etc.

The processor 130 may control the general operation of the user terminal apparatus 100-2 by using various modules stored in the storage 120.

The processor 130, as shown in FIG. 13, may include a random access memory (RAM) 131, a read-only memory (ROM) 132, a central processing unit (CPU) 133 (or multiple CPUs), a graphics processor 134, and first through n-th interfaces 135-1 through 135-n. The RAM 131, the ROM 132, the CPU 133, the graphic processing unit 134, and the first through n-th interfaces 135-1 through 135-n may be connected to each other via a bus 136.

The ROM 132 stores a set of commands for system booting. The CPU 133 copies various application programs stored in the storage 120 to the RAM 131, executes the application programs copied to the RAM 131, and performs various operations.

The CPU 133 accesses the storage 120 and performs booting by using an operating system (OS) stored in the storage 120. The CPU 133 performs various operations by using various programs, contents, data, etc., that are stored in the storage 120.

The graphics processor 134 generates a screen including various objects such as icons, images, text, etc. by using a computation unit and a rendering unit. The computation unit computes variables such as coordinate values, shapes, sizes, colors, etc. of objects that are to be displayed according to a layout of the screen. The rendering unit generates a screen of various layouts including objects based on the variables computed by the computation unit.

The audio processor 160 is a component that performs processing on audio data. However, processing the audio data may be performed by an audio processing module stored in the storage 120.

The audio output unit 170 is a component for outputting audio data processed by the audio processor 160. The audio output unit 170 may include a receiver terminal and a speaker.

The video processor 180 is a component for performing various image processing on content, such as decoding, scaling, noise filtering, frame rate converting, resolution converting, etc. However, video processing may be performed by a video processing module stored in the storage 120.

The user interface 190 is a component for sensing a user interaction for controlling the general operation of the user terminal apparatus 100-2. In particular, the user interface 190 may include various interaction sensing apparatuses such as a microphone, a keyboard, a mouse, a touch sensor, a motion sensor, etc.

Figure 16:
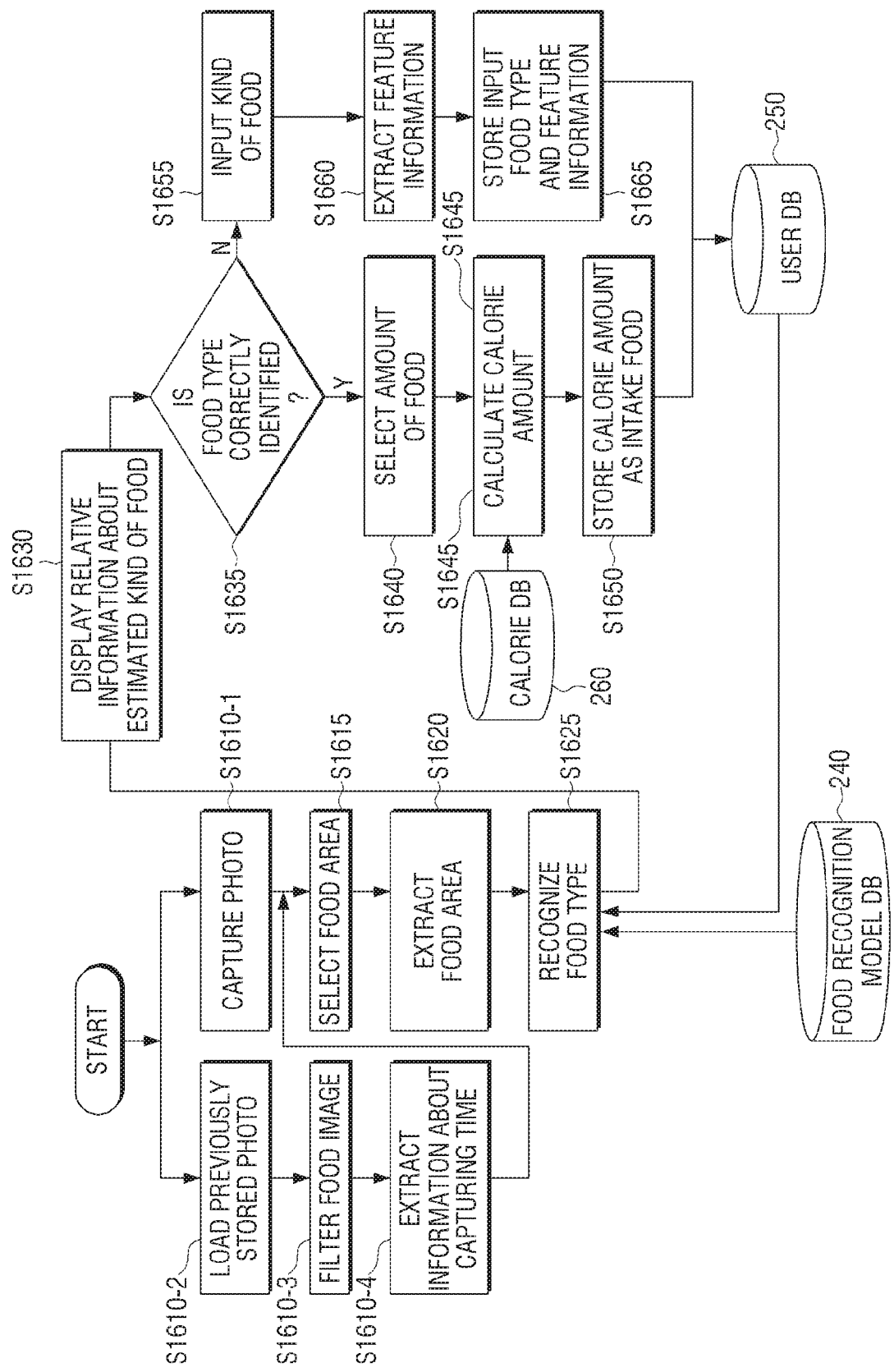
FIG. 16 is a flowchart illustrating an example process of determining a food type according to an exemplary embodiment.

FIG. 16 is a flowchart illustrating an example process of determining a food type according to an exemplary embodiment. For the sake of clarity, the method is described in terms of the exemplary user terminal apparatus 100 as shown in FIG. 1 configured to practice the method. However, the exemplary user terminal apparatus 100-1 as shown in FIG. 11 or the exemplary user terminal apparatus 100-2 as shown in FIG. 15 may also perform any of the steps disclosed herein. The steps outlined herein are exemplary and can be implemented in any combination thereof, including combinations that exclude, add, or modify certain steps.

Firstly, a captured image is obtained by capturing a photo through a camera included in the user terminal apparatus 100' (S1610-1). Capturing of the photo may be performed by executing a capturing application and may be performed by interacting with the capturing application according to a control command relating to capturing of a user on a healthcare application.

Alternatively, the captured image may be a previously stored captured image (i.e., a photo) obtained through the healthcare application (S1610-2). When the stored captured image is loaded, first filtering that selects captured images that include a food image from captured images based on feature information of the captured image may be performed (S1610-3). Also, information about capturing date and time of the corresponding captured image is extracted from EXIF data included in the captured image and is recorded as food eaten at the corresponding time (S1610-4).

The captured images on the healthcare application may be arranged and displayed on a UI in a timeline in which the captured images are aligned in the order of capturing time. At this time, the UI in a timeline may be configured whenever a captured image is obtained while the healthcare application is executed as background and may be configured by loading a stored captured image when the healthcare application is executed.

On a screen displaying the UI in a timeline, a user may select a region of the image related to the food item that the user has eaten from a captured image that includes a plurality of food types (S1615) and may extract the selected area of food (S1620).

The user terminal apparatus 100 may recognize or determine a food type by using feature information included in a food area from the extracted area of food and/or previously stored intake history information of the user (S1625). Specifically, the user terminal apparatus 100 may compare feature information of the food by using the food recognition model 240 stored in the external server 200, thereby estimating the food type. The user terminal apparatus 100 may preferentially recognize a food type to which a higher weight is applied based on the intake history information of the user stored in the user DB 250 by additionally using the user DB 250. Also, when the user terminal apparatus 100 receives detected food types corresponding to captured images as many as a preset number of times from the user and stores the food types as part of the intake history information, the user terminal apparatus 100 may determine the food types by using only the user DB 250. The intake history information stored in the user DB 250 of the external server 200 may be transmitted to and stored in the user terminal apparatus 100.

Thereafter, relevant information about an detected food type is displayed (S1630).

When the food type is determined, whether the food type is correctly identified may be confirmed by a user input (S1635). When the food type is correctly identified (S1635: Y), an amount of the identified food is selected (S1640), an intake calorie amount is calculated from the identified food type and the amount (S1645), and may be stored as intake history information (S1650). The intake calorie amount may be calculated by using the calorie DB 260 stored in the external server 200.

When the food type is not correctly identified (S1635:N), the food type may be directly input by the user (S1655), feature information of the captured image is extracted (S1660), and information that matches the extracted feature information and the food type input by the user may be stored in the user DB 250 of the external server 200 as par of a food intake history (S1665). At this time, among a plurality of food types having similar feature information to the extracted feature information, a high estimation weight may be applied to the matching food type and is stored for the user.

According to various exemplary embodiments as described above, a user may more conveniently input information about food that the user eats to an application executed in a user terminal apparatus and manage an eating habit.

The control method of the user terminal apparatus according to various exemplary embodiments may be implemented as programs which may be stored by various computer-readable media. That is, computer programs recorded on a computer-readable storage medium may be processed by various processors and may perform the above-described various control methods.

For example, a non-transitory computer-readable medium storing a program that performs an operation of obtaining a captured image, an operation of extracting a food image from the captured image, an operation of determining a food type included in the captured image based on feature information of the extracted food image and a previously stored food intake history, and an operation of displaying relevant information about the identified food type may be provided.

The non-transitory computer-readable medium does not include a medium storing data for a relatively short instance such as a register, a cache memory, RAM, etc. but may include a device-readable medium storing data permanently or semi-permanently. Specifically, the above-described various applications or programs may be provided by being stored in the non-transitory computer-readable medium such as a compact disc (CD), a digital versatile disc (DVD), a hard disk, a solid-state drive (SSD), a Blue-ray disc, a Universal Serial Bus (USB) memory device, a memory card, a ROM, etc.

Hereinabove, although various exemplary embodiments are separately described, each of the exemplary embodiments does not necessarily need to be solely implemented, but a configuration and an operation of each of the exemplary embodiments may also be implemented to be combined with one or more other exemplary embodiments. The word "exemplary" is used herein to mean "serving as an example or illustration." Any aspect or design described herein as "exemplary" is not necessarily to be construed as preferred or advantageous over other aspects or designs.

Hereinabove, although the exemplary embodiments have been shown and described, it should be understood that the present disclosure is not limited to the disclosed embodiments and may be variously changed without departing from the spirit and the scope of the present disclosure. Therefore, the present disclosure should be construed as including all the changes, equivalents, and substitutions included in the spirit and scope of the present disclosure.

What is claimed is:

1. An electronic device comprising:
    a display;
    a camera configured to obtain a captured image; and
    a processor configured to:
        execute an artificial intelligence (AI) automatic classifier configured to extract feature information of a food in the captured image, identify a type of the food in the captured image based on the feature information of the food in the captured image, and identify an amount of the food in the captured image based on the feature information, wherein the feature information comprises at least one of a color of the food in the captured image, a shape of the food in the captured image, and a texture of the food in the captured image;
        transmit information on the type of the food to an external server;
        obtain, from the external server, calorie information of the type of the food; and
        control the display to display an amount of calories of the food in the captured image based on the calorie information, the amount of the food in the captured image, and the type of the food in the captured image,
    wherein the calorie information of the type of the food comprises an amount of calories of the type of the food.

2. A control method of an electronic device, the control method comprising:
    obtaining a captured image;
    extracting feature information of a food in the captured image using an artificial intelligence (AI) automatic classifier executed by the electronic device, wherein the feature information comprises at least one of a color of the food in the captured image, a shape of the food in the captured image, and a texture of the food in the captured image;
    identifying a type of the food in the captured image based on the feature information of the food in the captured image using the artificial intelligence (AI) automatic classifier;
    identifying an amount of the food in the captured image based on the feature information using the artificial intelligence (AI) automatic classifier;
    transmitting information on the type of the food to an external server;
    obtaining, from the external server, calorie information of the type of the food; and
    controlling a display to display an amount of calories of the food in the captured image based on the calorie information, the amount of the food in the captured image, and the type of the food in the captured image,
    wherein the calorie information of the type of the food comprises an amount of calories of the type of the food.

3. A non-transitory computer-readable medium having recorded thereon a computer program for executing a method of controlling an electronic device, the method comprising:
    obtaining a captured image;
    extracting feature information of a food in the captured image using an artificial intelligence (AI) automatic classifier executed by the electronic device, wherein the feature information comprises at least one of a color of the food in the captured image, a shape of the food in the captured image, and a texture of the food in the captured image;
    identifying a type of the food in the captured image based on the feature information of the food in the captured image using the artificial intelligence (AI) automatic classifier;
    identifying an amount of the food in the captured image based on the feature information using the artificial intelligence (AI) automatic classifier;
    transmitting information on the type of the food to an external server;
    obtaining, from the external server, calorie information of the type of the food; and
    controlling a display to display an amount of calories of the food in the captured image based on the calorie information of the type, the amount of the food in the captured image, and the type of the food in the captured image,
    wherein the calorie information of the type of the food comprises an amount of calories of the type of the food.

* * * * *